United States Patent [19]

Demmer et al.

[11] Patent Number: 4,859,472
[45] Date of Patent: Aug. 22, 1989

[54] CLODRONATE-CONTAINING MEDICAMENTS AND A PROCESS FOR THE PREPARATION THEREOF

[75] Inventors: Fritz Demmer, Hirschberg-Leutershausen; Berthold Stemmle, Hockenheim, both of Fed. Rep. of Germany

[73] Assignee: Boehringer Mannheim GmbH, Mannheim, Fed. Rep. of Germany

[21] Appl. No.: 134,047

[22] Filed: Dec. 17, 1987

[30] Foreign Application Priority Data

Dec. 29, 1986 [DE] Fed. Rep. of Germany ....... 3643758

[51] Int. Cl.$^4$ ................................................ A61K 9/14
[52] U.S. Cl. ..................................... 424/489; 514/960
[58] Field of Search .......................... 424/489; 514/960

[56] References Cited

U.S. PATENT DOCUMENTS

| | | | |
|---|---|---|---|
| 4,159,346 | 6/1979 | Omura et al. | 514/960 |
| 4,614,648 | 9/1986 | Bru | 514/960 |
| 4,687,662 | 8/1987 | Schobel | 514/960 |

FOREIGN PATENT DOCUMENTS 0015370 9/1980 European Pat. Off. .

*Primary Examiner*—A. Lionel Clingman
*Assistant Examiner*—Willie J. Thompson
*Attorney, Agent, or Firm*—Armstrong, Nikaido, Marmelstein, Kubovcik & Murray

[57] ABSTRACT

The present invention provides a medicament containing 80 to 95% clodronate, 2 to 10% filling material and 1 to 10% lubricant.

The present invention also provides a process for the production of a clodronate-containing medicament containing 80 to 95% clodronate, 2 to 10% filling material and 1 to 10% lubricant, wherein the dry components are mixed, moist granulated with an aqueous binding agent and the granulate obtained subsequently dried, a lubricant being additionally admixed with the final granulate in an amount of from 1 to 5% and the mixture thus obtained pressed into tablets or filled into capsules which have a rate of dissolving of >90% after 30 minutes.

21 Claims, No Drawings

CLODRONATE-CONTAINING MEDICAMENTS AND A PROCESS FOR THE PREPARATION THEREOF

The present invention is concerned with clodronate-containing medicaments with an active material content of 80 to 95% and a process for the preparation thereof.

Sodium clodronate is a short chemical name for methane-dichlorodiphosphonic acid disodium salt. It is known that this compound can be used in medicaments for preventing anomalous mobilisation and deposition of calcium phosphate in animal and human tissues (cf. Federal Republic of Germany Patent Specification No. 18 13 659). Since this compound must be administered in relatively high dosages for a long period of time in order to manifest its action, for convenient administration it is necessary to have a medicinal form for oral administration with a high content of active material, i.e. a comparatively small tablet size. Usual tablet formulations, such as are described for similar materials in, for example, the above-mentioned Federal Republic of Germany Patent Specification No. 18 13 659, prove, surprisingly, to be useless since the corresponding products, because of the properties of clodronate, tend either to adhere to the matrix wall of the automatic filling machine and thus prevent a satisfactory dosing or, in the case of a capsule machine, stick to the dosing or ejection plungers so that even comparatively thick coatings can form and the dosage is again insufficient.

Therefore, the problem exists of developing a formulation for clodronate which combines a high concentration of active material, on the one hand, with good working up properties in automatic filling machines, on the other hand, without the dissolving speed of the finished preparations or the bioavailability of the preparations suffering.

According to the present invention, the problem is solved by preparing medicaments with a content of 80 to about 95% clodronate, 2 to 10% of filling materials and 1 to 10% of lubricant.

Especially preferred embodimental forms for these medicaments are tablets and capsules.

As a rule, the content of active material is in the range of from 400 to 1000 mg. per individual dosage unit.

The medicaments according to the present invention contain clodronate in an amount of from 80 to 95% of the total mixture, referred to anhydrous clodronate. It is preferable to use the disodium salt, which can be employed in the form of its tetrahydrate but can also be used in anhydrous form. Of course, use can also be made of other physiologically acceptable salts, for example the lithium, potassium, ammonium or calcium salt, or also of the free acid, optionally in combination with an appropriate buffer. Whereas for the achievement of a rapid liberation of active material, it is usual to work with an active material which is as fine grained as possible, i.e. ground, according to the present invention, an unground product can be used which also contains particles with a size of more than 400 μm., in which case at least 70% has a particle size of less than 400 μm. and preferably of less than 200 μm.

The formulation also contains filling materials in an amount of from about 2 to 10%. As such, there can be used starch, lactose, glucose, mannitol, calcium carbonate, calcium phosphate, cellulose or other products known in the technology for this purpose. In order to bring the speed of dissolving into the desired liberation range of from 15 to 30 minutes for an in vitro dissolving rate of more than 60% or of more than 90%, respectively, a disintegration agent is added in an amount of from 2 to 10%. As disintegration agents, there have proved to be especially useful carboxymethylstarch and carboxymethylcellulose, as well as silica gel. However, it is also possible to use other products acting in the same manner. Furthermore, the formulation can contain a lubricant in an amount of from 0 to 5%.

According to the present invention, the abovementioned components are mixed dry and then moist granulated with a conventional binding agent, such as starch paste or also only with water. The dried granulate should have a grain size of from 0.1 to 2 mm. and preferably of about 1 mm. For further working up, a lubricant is again mixed with this granulate in an amount of from 1 to 5%, in which case magnesium stearate, talc, paraffin, aluminium hydroxysilicate, lubricating oil or similar products can be used. A mixture of equal amounts of talc and magnesium stearate is especially advantageous. However, it is also possible to use different proportions in this mixture. The total content of active material in the so produced granulates is only slightly reduced by the again added amount of lubricant to about 1 to 2%. The percentage proportion of lubricants in the final medicament is from 1 to 10% and preferably from 4 to 8%, a range of from 5 to 7% having proved to be especially advantageous.

This mixture, which can readily be filled on automatic devices, can subsequently be pressed into tablets or filled into conventional gelatine capsules. Tablet and capsule sizes are preferably so chosen that they contain an active material concentration of 400 to 1000 mg. per dosage unit. It is also possible first to produce pellets or minitablets and subsequently to fill these into capsules to give larger dosage units, for example containing >500 mg. of active material, or into sachets or containers. The formulations with the composition according to the present invention can be satisfactorily produced, give readily flowing and fillable granulates which, in the case of pressing or of filling into capsules, do not adhere to the tools used. Thus, a satisfactory dosaging of an individual dosage unit can be achieved with a deviation of less than 2% and normally of less than 1% from the desired weight.

An important criterion for the quality of the medicaments according to the present invention is the rate of dissolving of an individual dosage unit. In the determination of the dissolving rate (U.S.P. paddle method), it was ascertained that the formulation according to the present invention had already dissolved after 15 minutes to an extent of more than 60% and after 30 minutes to an extent of more than 90%, whereas a formulation with a content of lubricant of about 8% displayed a dissolving rate of less than 30% and of less than 60%, respectively.

The following examples, which are given for the purpose of illustrating the present invention, describe the production of the medicaments according to the present invention, as well as of comparative products:

EXAMPLE 1.

Standard formulation I.

| | |
|---|---|
| 1. sodium clodronate tetrahydrate | 500 mg. |
| 2. talc | 23 mg. |
| 3. maize starch | 15 mg. |
| 4. sodium carboxymethylstarch | 10 mg. |

-continued

| 5. magnesium stearate | 2 mg. |
|---|---|
| | 550 mg. |

Standard formulation II.

| 1. anhydrous sodium clodronate | 400 mg. |
|---|---|
| 2. talc | 18 mg. |
| 3. maize starch | 12 mg. |
| 4. sodium carboxymethylstarch | 8 mg. |
| 5. magnesium stearate | 2 mg. |
| | 440 mg. |

(1) Batch size: 200,000 pieces

A. Mix 1. and 2. and granulate with a 15% paste of 3. and water in a granulator (e.g. Diosna), dry and sieve.

B. Mix 4. and 5. with granulate from A.

The granulate obtained flows readily but, after a short time, a coating is formed on the dosaging tubes and on the ejection plungers of the filling machine which prevents a satisfactory dosaging.

(b) Batch size: 10,000 pieces

A. Mix 1. through 3. and granulate with water in a granulator (e.g. Diosna), dry and sieve.

B. Mix 4. and 5. with granulate A.

The flowability is insufficient and comparatively large dosage variations are unavoidable.

EXAMPLE 2.

To the granulate (1–3) produced according to Example (1a) are additionally added to 4. and 5. a (a) 2.5 mg. magnesium stearate and 2.5 mg. talc in an amount of about 1%.

(b) 5 mg. magnesium stearate and 5 mg. talc in an amount of about 2%

(c) 10 mg. magnesium stearate and 10 mg. talc in an amount of about 4%.

The granulates obtained according to (a) and (b) have a satisfactory flowability and can be filled with the use of automatic filling machines.

By further increasing the addition of lubricant to 4% (see above under (c)) so that, together with the amount of 4% already present in the formulation I, there is obtained a total amount of lubricant of 8%, there are also obtained readily workable granulates which, however, display in the final formulation an insufficient rate of dissolving (cf. the following Table):

TABLE

| Example No. | lubricant addition | rate of dissolving | | VC % variation | |
|---|---|---|---|---|---|
| | | 15 min. | 30 min. | 15 min. | 30 min. |
| 1a | — | — | — | — | — |
| 1b | — | — | — | — | — |
| 2a | 5 mg. | 88 | 99 | 1.8 | 1.3 |
| 2b | 10 mg. | 69 | 103 | 2.2 | 0 |
| 2c | 20 mg. | 26 | 58 | 62.3 | 33.3 |

In the above working examples, standard formulation I was utilized in Example 1 and Example 2, but standard formulation II could be interchanged therewith without significant change to the reported results.

As reported in the working examples, Examples 1(a) and (b), as well as Example 2(c) are outside of the scope of the present invention.

We claim:

1. Process comprising mixing together (80–95%) by weight of methanedichlorodiphosphonic acid or a physiologically acceptable salt thereof (2 to 10%) by weight of pharmaceutically acceptable filler 0 to 10% by weight of pharmaceutically acceptable disintegration agent 0 to 5% by weight of a first pharmaceutically acceptable lubricant, to form a mixture, granulating and drying the first mixture, mixing 1 to 5% by weight of pharmaceutically acceptable second lubricant with the dried first mixture to form a second mixture containing 1 to 10% by weight of pharmaceutically acceptable lubricant, and forming the second mixture into a unit dose form having a rate of dissolving of greater than 90% after 30 minutes.

2. Process of claim 1, wherein the first mixture is granulated with an aqueous binding agent.

3. Process of claim 2, wherein the aqueous binding agent is 2.5 to 20% by weight of starch.

4. Process of claim 3, wherein said second lubricant is magnesium stearate and talc.

5. Process of claim 1, wherein said first and second lubricants are the same.

6. Process of claim 1, wherein the clodronate is in the form of a tetrahydrate.

7. Process of claim 1, wherein at least 70% of the clodronate has a particle size less than 400 mm.

8. Process of claim 7, wherein at least 70% of the clodronate has a particle size less than 200 mm.

9. Process of claim 1, wherein the filler is starch, lactose, glucose, mannitol, calcium carbonate, calcium phosphate or cellulose.

10. Process of claim 1, wherein the first mixture contains 2 to 10% by weight of a pharmaceutically acceptable disintegration agent.

11. Process of claim 1, wherein the dried granulate has a grain size of from 0.1 to 2 mm.

12. Process of claim 1, wherein the first and second lubricants are independently selected from the group consisting of magnesium stearate, talc, paraffin, aluminum hydroxysilicate, and pharmaceutically acceptable lubricating oil.

13. Composition for preventing anomalous mobilization and deposition of calcium phosphate in mammal tissues, said composition comprising 80 to 90% by weight of methanedichlorodiphosphonic acid or a physiologically acceptable salt thereof 2 to 10% by weight pharmaceutically acceptable filler 5 to 7% by weight pharmaceutically acceptable lubricant.

14. Composition of claim 13, wherein the composition is in the form of tablets or capsules.

15. Composition of claim 13, wherein the composition is in the form of dosage units, wherein each dosage unit contains from 400 to 1000 mg of methanedichlorodiphosphonic acid or a physiologically acceptable salt thereof.

16. Composition of claim 13, wherein in the U.S.P. paddle method more than 60% of the composition dissolves in water after 15 minutes, and more than 90% of the composition dissolves after 30 minutes.

17. Composition of claim 13, wherein the clodronate is selected from the group consisting of sodium, lithium, potassium, ammonium and calcium clodronate salts and the free acid form of clodronate.

18. Composition of claim 13, additionally containing 2 to 10% by weight of a pharmaceutically acceptable disintegration agent.

19. Composition of claim 13, wherein each dosage unit contains about 500 mg of sodium clodronate tetrahydrate 10 mg of sodium carboxymethyl starch 15 mg of maize starch, 23 to 28 mg of talc and 2 to 7 mg of magnesium stearate.

20. Product produced by the process of claim 1.

21. Process of claim 1, wherein the unit dose form is formed in an automatic filling machine.

* * * * *

UNITED STATES PATENT AND TRADEMARK OFFICE
CERTIFICATE OF CORRECTION

PATENT NO. : 4,859,472

DATED : August 22, 1989

INVENTOR(S) : DEMMER et al

It is certified that error appears in the above-identified patent and that said Letters Patent is hereby corrected as shown below:

On the cover page, Item [30], "Dec. 29, 1986" should read --Dec. 20, 1986--.

Signed and Sealed this

Second Day of October, 1990

Attest:

HARRY F. MANBECK, JR.

*Attesting Officer*          *Commissioner of Patents and Trademarks*